United States Patent
Salamone et al.

(10) Patent No.: US 8,329,416 B2
(45) Date of Patent: Dec. 11, 2012

(54) STABILIZED STANDARDS FOR BUSULFAN IMMUNOASSAY

(75) Inventors: Salvatore J. Salamone, Stockton, NJ (US); Jodi Blake Courtney, Doylestown, PA (US); Yunying Li, Phillipsburg, NJ (US)

(73) Assignee: Saladax Biomedical Inc., Bethlehem, PA (US)

( * ) Notice: Subject to any disclaimer, the term of this patent is extended or adjusted under 35 U.S.C. 154(b) by 0 days.

(21) Appl. No.: 13/226,874

(22) Filed: Sep. 7, 2011

(65) Prior Publication Data

US 2012/0225443 A1 Sep. 6, 2012

Related U.S. Application Data

(62) Division of application No. 12/212,160, filed on Sep. 17, 2008, now Pat. No. 8,039,220.

(51) Int. Cl.
*G01N 33/53* (2006.01)
*C07K 16/00* (2006.01)
*C07K 1/10* (2006.01)

(52) U.S. Cl. ............ 435/7.1; 435/7.93; 530/389.8; 530/402; 436/56; 436/8

(58) Field of Classification Search .............. None
See application file for complete search history.

(56) References Cited

OTHER PUBLICATIONS

Peris et al. Determination of busulfan in human plasma using high-performance liquid chromatography with pre-column derivatization and fluorescence detection. Journal of Chromatography B, 1999, vol. 730, pp. 33-40.*

* cited by examiner

*Primary Examiner* — Shafiqul Haq

(57) ABSTRACT

Use of busulfan amide as stabilized standards in immunoassays for quantifying the amount of busulfan in samples of human biological fluids, methods for carrying out said immunoassay and kits for use in said immunoassay.

3 Claims, 3 Drawing Sheets

STABILIZED STANDARDS FOR BUSULFAN IMMUNOASSAY

CROSS REFERENCE TO RELATED APPLICATION

This Application is a Divisional Application of application Ser. No. 12/212,160 filed Sep. 17, 2008 now U.S. Pat. No. 8,039,220.

FIELD OF THE INVENTION

This invention relates to the field of standards for immunological assays to quantify the amount of busulfan in human biological fluids to rapidly and accurately determine optimal drug concentrations in patient samples during chemotherapy.

BACKGROUND OF THE INVENTION

Cancer is a term used to describe a group of malignancies that all share the common trait of developing when cells in a part of the body begin to grow out of control. Most cancers form as tumors, but can also manifest in the blood and circulate through other tissues where they grow. Cancer malignancies are most commonly treated with a combination of surgery, chemotherapy, and/or radiation therapy. The type of treatment used to treat a specific cancer depends upon several factors including the type of cancer malignancy and the stage during which it was diagnosed.

Busulfan is a common cytotoxic agent that is used for the treatment of chronic myelogenous leukemia and high-dose pre-transplant conditioning. This chemotherapeutic agent has the formula:

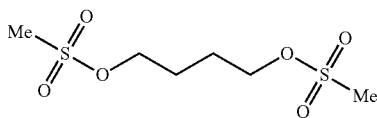

I

This compound has been associated with debilitating side effects such as mucositis, hepatic veno-occlusive disease and myelosuppression. By monitoring the levels of busulfan in the body and adjusting the dose, these side effects can be better controlled and limited in patients.

Routine therapeutic drug management of busulfan requires the use of simple automated tests such as immunoassays which are adaptable to general laboratory equipment. In general these immunoassay are performed on fluid samples taken from a patient who is being treated with the busulfan so as to monitor his therapy. In so doing the health facilities, such as hospitals, laboratories and doctors offices use immunoassays by means of kits for performing such immunoassays. In order to carry out these assays, kits containing reagents, standards and instructions for carrying out the immunoassay are provided by their manufacturer. In this way the immunoassay can be performed at these health facilities. These kits usually contain the necessary reagents in separate containers for carrying out the busulfan immunoassay on the patient samples.

In order to quantify the amount of busulfan in a patient sample, a set of standards, each standard containing a known amount or concentration of busulfan, are placed in the assay kit or in a separate calibration kit to correlate the results of the immunoassay on the patient sample with the results achieved through subjecting the standards containing known amounts or known concentrations of busulfan to the same immunoassay to which the sample was subjected. In these kits the set of standards contains a sufficient number of standards of different concentration of busulfan, so that when all of the standards are subjected to the immunoassay, the results achieved with respect to the all of the standards can be plotted against the different concentrations to provide a curve or a straight line.

In this manner by means of this immunoassay, the results with respect to the patient's sample can be compared and correlated through this plot to the results achieved by means of these standards with known concentrations of the busulfan. Locating on this plot, where the results obtained with the patent sample fall, will determine the amount of busulfan in the patient samples.

A major flaw in these kits or in the calibration kits for determining busulfan in a patient's sample is that the busulfan in the standard is unstable and after a prolonged period of time decomposes. Busulfan is a bifunctional alkylating agent that has two labile methanesulfonate groups that are attached at the opposite ends of a saturated four carbon chain. These two groups are readily hydrolyzed in aqueous media especially in the presence of nucleophiles. Studies have shown that busulfan decomposes significantly at 37° C. with a half life of 14 hours. At room temperature for 5 days, more than 60% of busulfan is decomposed.

In developing calibrators or controls of busulfan for use as standards in a quantitative assay, special care has to be taken so that the busulfan does not decompose and give inaccurate results. In practice calibrator matrix material is spiked at various levels with busulfan and the material is then aliquoted into smaller vials and frozen at −20° C. When an assay needs to be run, one of the aliquots is thawed and used in the assay that day. It cannot be keep at room temperature for more than a few hours and even at 4° C. the calibrator decomposes within a day. This adds a complexity and expense to laboratories in addition to causing doubt on the results due to the decomposition of the material used as a calibrator. The instability of busulfan calibrators and controls can often lead to erroneous results. Therefore having a stabilized material for use as a standard would allow for a great ease of use and more confidence in the results.

SUMMARY OF INVENTION

Figure 1:
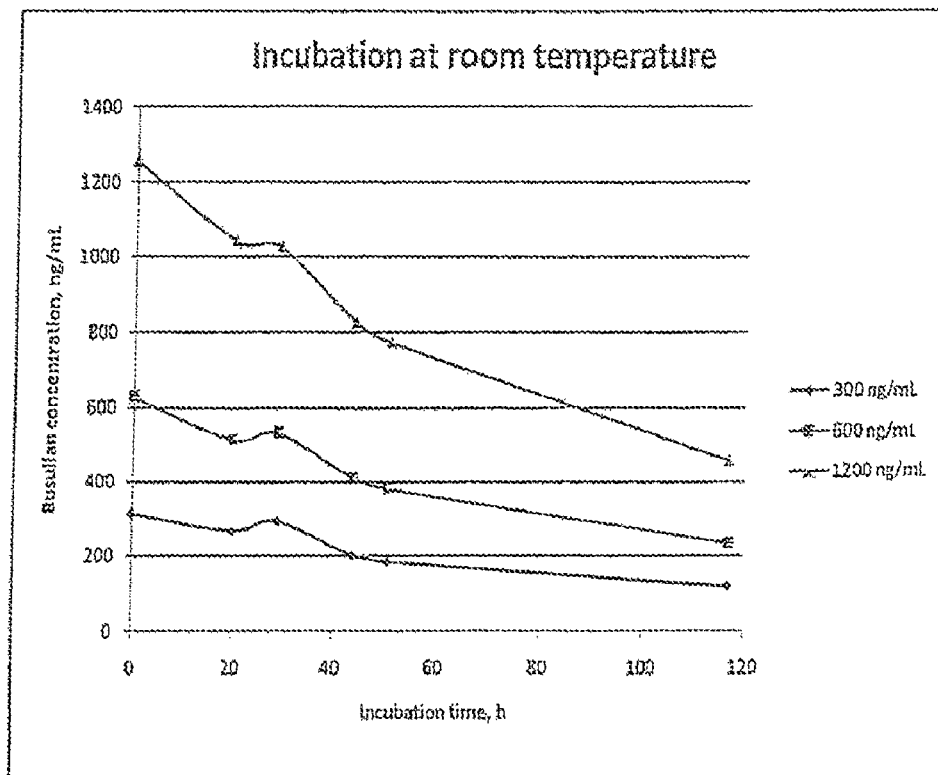
FIG. 1 is a graph demonstrating the decomposition of various busulfan standards when incubated over time at 37° C.

In accordance with this invention, it has been discovered that an amide of the formula:

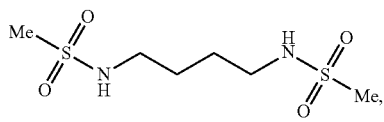

II is stable and does not decompose upon standing and produces results which when subjected to a busulfan immunoassay, correlate and correspond to the results achieved with known concentrations of busulfan, when subjected to the same busulfan immunoassay. This correlation and correspondence makes the stable compound of formula II ideally suited for use as standards as a substitute for busulfan, either in busulfan immunoassay kits or in calibration kits for performing busulfan immunoassays.

Therefore, the use of the amide of formula II in standards in busulfan immunoassays provides an effective method to measure and quantify the amount of busulfan in the sample. In accordance with this invention, a method is provided for quantifying the amount of busulfan in the human biological fluid by carrying out an immunoassay on said sample to measure the amount of busulfan in said sample and by carrying out an immunoassay on a set of standards containing known amounts of the amide of formula II to measure the amount of amide in the standard. By comparing and correlating the results obtained with the sample with results obtained with these standards, one can determine the amount of busulfan in the sample.

One means for comparing and correlating these results is through a plot of the results obtained from these standards containing different predetermined concentrations of the amide of formula II against the different predetermined concentrations of the amide of formula II in these standards. In order to compare and correlate the results both the standards and the sample have to be subjected to the same immunoassay. This is carried out by first comparing the measured results obtained from the sample with the measured results obtained from the plurality of standards containing the amide of formula II. The measured result obtained by this comparison can be correlated with know results obtained with busulfan containing standards and amount of busulfan in the sample determined. Therefore, the provision of a set of standards utilizing different predetermined concentrations of the amide of this invention provide an effective means for carrying out a busulfan immunoassay to determine the amount of busulfan in a sample of a patient treated with busulfan so as to effectively monitor the patient's therapy.

Also this invention includes its kits for carrying out a busulfan immunoassay and kits for calibrating the results of this immunoassay, all of which contain a set of standards containing varied concentrations or amounts of the amide of formula II.

DETAILED DESCRIPTION

In accordance with this invention, it has been found that stabilized busulfan standards containing different known concentration of the amide of formula II when subjected to busulfan immunoassay produce results which correlate and correspond to the results achieved by utilizing known concentrations of busulfan as the standard in the same busulfan immunoassay. Furthermore, due to their long-term stability, the standards containing the amides of formula II are ideally suited for placement in busulfan immunoassay kits or in kits for calibrating busulfan immunoassays. It is through the use of the standards containing the amide of formula II in immunoassay kits that an accurate immunoassay for quantifying busulfan in blood, plasma or other body fluid samples has been developed for use at health care facilities. By use of these standards, the amount of busulfan in body fluids, preferably in a blood or plasma sample, can be quantified. In this manner, a patient being treated with busulfan can be monitored during therapy by immunoassays carried out at health facilities or where the patient is being treated with busulfide so that the patient so treated can be monitored during therapy and his treatment adjusted in accordance with said monitoring.

Figure 2:
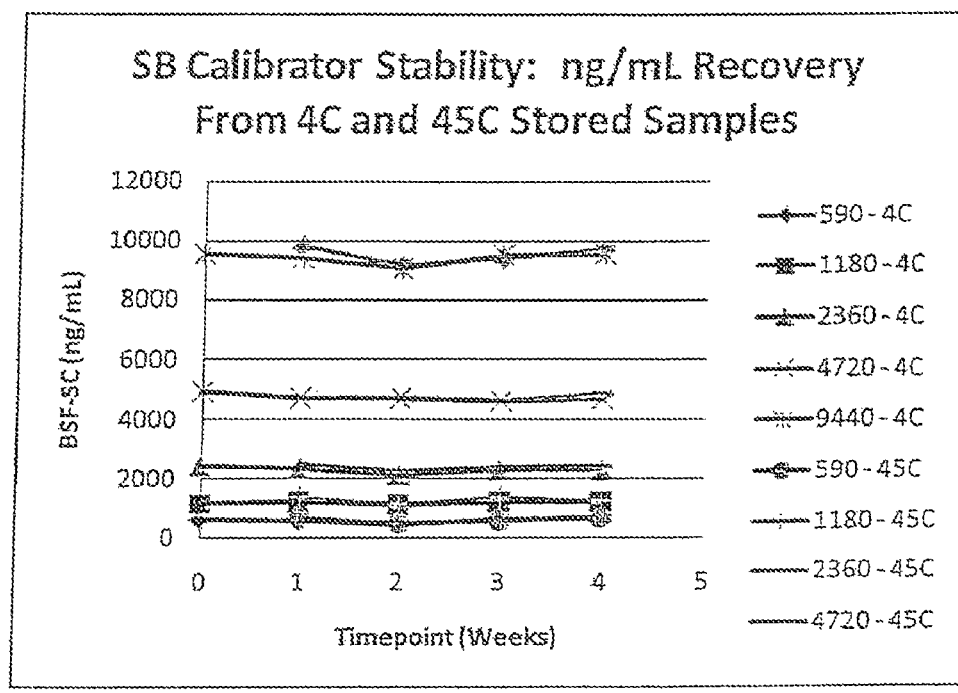
FIG. 2 is a graph demonstrating the stability over 4 weeks of standards formed with the amide of formula II in accordance with this invention.

The instability of busulfan and the stability of the amide of formula II is demonstrated by comparing the results in FIG. 1 with the results in FIG. 2. In FIG. 1 a plurality of aqueous solutions of busulfan having varying concentrations of 100 ng/ml, 600 ng/ml, and 1200 ng/ml are incubated at room temperature. As seen from FIG. 1, busulfan decomposes significantly at 37° C. with a half life of 14 h. At room temperature for 5 days, more than 60% of the busulfan is decomposed. FIG. 2 shows stability tests with regard to a plurality of varying concentrations of the amide of formula II in clear solutions, at different concentrations ranging from 590 ng/ml to 4720 ng/ml. As seen from the results n FIG. 2, the amide of formula II is stable at 4° C. and 45° C. for at least 4 weeks. FIG. 2 shows no decomposition of the amide of formula II, even after these solutions are stored at 4° C. and 45° C. for at least 4 weeks. In fact these amide solutions can be stored for more than one year without any significant deterioration and without any special precautions.

The set of standards of this invention containing various concentrations of the amide of formula II can be utilized in accordance with any conventional method for carrying out a busulfan immunoassay to determine and quantify busulfan in blood, plasma or other body fluid samples. However it is important that the standards of this invention be subjected to the same immunoassay utilizing the same method and same reagents as used in the immunoassay on the patients sample. Any of the conventional busulfan assay reagents can be utilized in such busulfan immunoassay and in preparing the kits for carrying out the busulfan immunoassay which contain the set of standards of this invention.

Generally these immunoassays are carried out utilizing antibodies which are reactive with busulfan. Both either direct competitive or indirect competitive assays can be utilized. In these immunoassays, binding with a given antibody can be measured by the amount of busulfan which either binds or is not bound to the antibody. Indirect competitive assays generally measure the amount of antibody which is not bound to the busulfan label. Competitive assays generally utilize conjugates which are binding partners with the busulfan present in the sample for binding to the antibodies. Therefore, in competitive assays, binding to the antibody can be measured by the amount of conjugate reagent which binds to the antibody which will be inversely proportional to the amount of busulfan in the sample.

The amount of busulfan in the sample is generally determined by correlating the measured amount of the bound or unbound conjugate produced by the busulfan sample with the values of the bound or unbound conjugate from a set of standards. In the past these standards contained various known amounts of busulfan. One manner of correlating the value of the measured amount produced by the sample is through plotting these values of the standards against the various known concentrations of busulfan in the standards to produce a straight line or a curve. These studies for producing calibration plot are determined using the same immunoassay procedure for the standards as used for the sample. In accordance with this invention, standards containing various known concentrations of the amide of formula II are substituted for the busulfan containing standards in this procedure In accordance with a preferred embodiment of this invention, a competitive assay is provided utilizing the reagents and procedure disclosed in U.S. Pat. No. 7,148,024, whose disclosure is incorporated by reference In this preferred procedure, the preferred procedure as set forth in U.S. Pat. No. 7,148,024, utilized in its method antibodies produced from conjugates of an immunogenic polyamine polymer with a compound of the formula III-A:

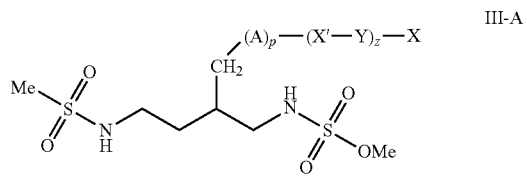

wherein A is lower alkylene;
X' is a functional linking group;
Y is an organic spacing group;
X is a terminal functional group capable of binding to a polyamine polymer;
p and z are independent integers of from 0 to 1;
compounds of the formula III-B

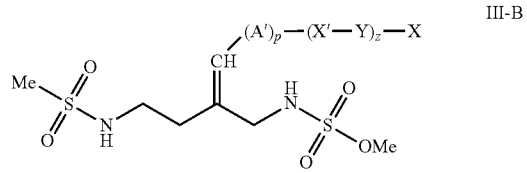

wherein A' is lower alkylene or lower alkenylene;
X', Y, X, p and z are as above
or mixtures thereof. The antibodies so produced are specific for busulfan and do not substantially react with or bind to the blocking metabolites of busulfan, which are tetramethylene sulfone, tetrahydrothiophene and tetrahydrothiophene-3-ol-1,1-dioxide. The procedure of U.S. Pat. No. 7,148,024 utilizes a new class of antibodies is provided which substantially selectively reacts with busulfan and do not substantially react or cross react with the busulfan metabolites mentioned hereinabove.

It has been discovered that through the use of these α-substituted busulfan derivatives of formulae III-A and III-B as immunogens, this class of antibodies are provided. It is the use of these antibodies that provides an accurate immunoassay, for detecting and/or quantifying busulfan in blood, plasma or other body of busulfan in cancer patients being treated with busulfan as a chemotherapeutic agent.

The reagents utilized in the assay of this invention include conjugates of a polymeric carrier with the compounds of formulae III-A and III-B. These conjugates are competitive binding partners with the busulfan present in the sample for the binding with these antibodies. Therefore, the amount of conjugate reagent which binds to the antibody will be inversely proportional to the amount of busulfan in the sample.

The method of this invention for quantifying the amount of busulfan in a human biological fluid sample utilizes a set of new and improved stabilized standards containing various known concentrations of the amide of formula II. This method is carried out by first subjecting the sample to a busulfan immunoassay, preferably an immunoassay which utilizes an antibody reactive with busulfan, to obtain a result which corresponds to the amount or concentration of busulfan in this sample. This result is then compared to the measured results obtained from a plurality of standards; each standard containing a different concentration of amide of formula II.

In order to carry out the method of this invention, each of the standards has to be subjected to the same immunoassay as said sample. In this manner, results are obtained which correspond to the amount or concentration of the amide of formula II in each of the standards. Any of the conventional methods of quantifying the amount or concentration of a hapten in a body fluid from the measured result of an immunoassay by comparing and correlating this result with the measured result obtained from a plurality of standards of varying concentration can be used in accordance with this invention. In accordance with a preferred embodiment, the measured result obtained from the sample by the immunoassay is compared with the measured results obtained from the plurality of standards, each containing a varying amount or concentration of amide of formula II, as a means for quantifying the amount or concentration of busulfan in said sample. Determining where the measured result obtained from the immunoassay of the sample falls within the parameter of measured results obtained from the plurality of standards forms the basis for quantifying the amount or concentration of busulfan in the sample.

In order provide an ease of comparisons by means of the use of the standards of this invention, a plurality of standards which contain solutions of the amide of formula II in a liquid carrier are supplied, each containing a different concentration or amount of the amide of formula II in the liquid carrier. In this preferred embodiment, there should be a sufficient number of standards so that when they are subjected to a busulfan immunoassay, the measured results of the immunoassay when plotted against each of the concentrations or amounts of the amide of formula II in the standards generate a curve or a straight line. Where the measured results of the immunoassay of the standards when plotted against the known concentrations of the amide of formula II in said standards generate a curve or a straight line, this plot can be used for ease and simplicity in quantifying the amount or concentration of busulfan in the sample. This is achieved by determining where the measured result of the busulfan immunoassay of the sample falls within the curve or straight line generated by the values of the measured results plotted for the standard.

In the preferred embodiment, the set of standards supplied should in sufficient number of varying known predetermined concentrations of the amide of formula II so that the measured results obtained from the busulfan immunoassay when plotted against known concentration of the amide of formula II in the standard generate a straight line or a curve. However any other means of comparing the measured result of the sample with the measured results of standards, such as by visualization, can be utilized in the method of this invention for quantifying the concentration or amount of busulfan in the human sample.

In accordance with the preferred embodiment, if the results of subjecting three standards to said busulfan immunoassay generate a straight line, then the number of standards that need be utilized may only be three. While three may only be necessary, more standards may be provided and subjected to immunoassay. When the plot of the measured results achieved by subjecting the standards to said immunoassay against the known concentrations of the amide formula II in said standards, the number of standards would be greater than three. However, generally it is preferred that there be from about three to ten standards, each containing different amounts or concentrations of the amide of formula II. While more than ten may be provided and subjected to a busulfan immunoassay, providing these large number of standards is generally uneconomical and achieves no beneficial purpose. In any event, the number of standards each containing a different amount or concentration of the amide of formula II provided in accordance with a preferred embodiment should be at least sufficient so that when these measured results obtained from the immunoassay are plotted against the known concentration or amounts of said amide in said standards, a straight line or curve is generated. In this plurality of standards, the preferable concentration of the amide of formula II in each of said standards is in a range of from about 0 to 16,000 ng/ml. Concentrations of greater than 16,000 ng/ml of amide of Formula II may be utilized. However it is seldom desired to utilize this amide in such high concentrations since these high concentrations generally exceed the concentration of busulfan in patient's samples.

In carrying out the busulfan immunoassay of the sample and the standards, it is necessary that the same busulfan immunoassay be used, which includes both the same reagents and same antibody. The sample and standards should be subjected to the same immunoassay technique. Usually these standards are supplied in the form of a inert liquid medium containing an inert solvent for the amide of formula II so that a given concentration of the amide of formula II is achieved. Any conventional inert liquid medium, including an inert solvent generally utilized in immunoassay standards, can be utilized in preparing the standards of this invention.

In preparing these standards containing the amide of formula II in different amounts or concentrations, these standards are calibrated with the known standards of busulfan prior to their placement in a kit and use in an immunoassay to obtain a busulfan equivalence factor. In accordance with this invention it is found that the concentrations of the amide of formula II produce measured results when subjected to a busulfan immunoassay are the same so as to correspond with the concentrations of busulfan when subjected to the same immunoassay. This busulfan equivalence factor is determined by subjecting solutions containing different concentration the amide of formula II and the busulfan to busulfan immunoassay and obtaining measured results for each of the concentrations of the busulfan and the amide by means of this immunoassay. From these measured results one can determined which concentration of this amide corresponds to the concentration of the busulfan in that it produces the same measured result. By correspondence, it is meant that the measured results is substantially the same at both concentrations of the amide and busulfan. Therefore, from these results, the concentration of the amide and the concentration of the busulfan which produces substantially the same measured results by this amino acid can be determined and the busulfan equivalent factor of the amide can be calculated. This calculation can be carried by the of a fraction with the numerator being the concentration of amide which produces the same measured result and the denominator being the concentration of busulfan which produces this same result. This result produces the busulfan equivalence factor which is generally constant through out the range of concentrations of the amide of formula II in solution in the standards. It is this correspondence which allows the amide of formula II to be used in the standards as a calibrator or control in place of busulfan in an immunoassay and busulfan immunoassay kit. This determination of the busulfan equivalence factor is carried out by the manufacturer or supplier before delivery to the healthcare facility.

The busulfan equivalence factor for each of standards supplied with the immunoassay kit is generally predetermined by a correlating immunoassay which is carried out before carrying out the immunoassay for which the kit is supplied. The information as to the busulfan equivalence factor can be supplied with the instructions for using the kit. On the other hand each of the standards containing different predetermined concentrations of amide of Formula II can be labeled with a number obtained by multiplying the concentration of amide of Formula II in the standard with the predetermined busulfan equivalence factor. This allows for the measured results from the immunoassay when carried out with the kit with the supplied standards containing various known concentrations of amide of formula II to be correlated with the measured results of this same immunoassay if it were carried out with a set of standards containing various known concentrations of busulfan.

The busulfan equivalence factor is obtained from the measured results obtained from a correlating immunoassay which is carried out before preparing the kit for carrying out immunoassays on patients' samples for which the kit is designed. This correlating immunoassay is carried out with standards containing various known concentrations of the amide of formula II and comparing the measured results thus obtained with the measured results of carrying out this correlating immunoassay with a set of standards containing various known concentrations of busulfan. In accordance with this invention it has been found that the amide of formula II produces measured results which when subjected to a busulfan immunoassay correspond to the concentrations of busulfan when subjected to the same immunoassay produce a busulfan equivalence factor which is constant through out the range of concentrations of the amide of formula II in solution in the standards. Therefore the step of comparing can be carried out by plotting said measured results obtained from the immunoassay of the sample with said plurality of standards against the known concentrations of said amide in said first set of standards multiplied by the busulfan equivalence factor.

Figure 3:
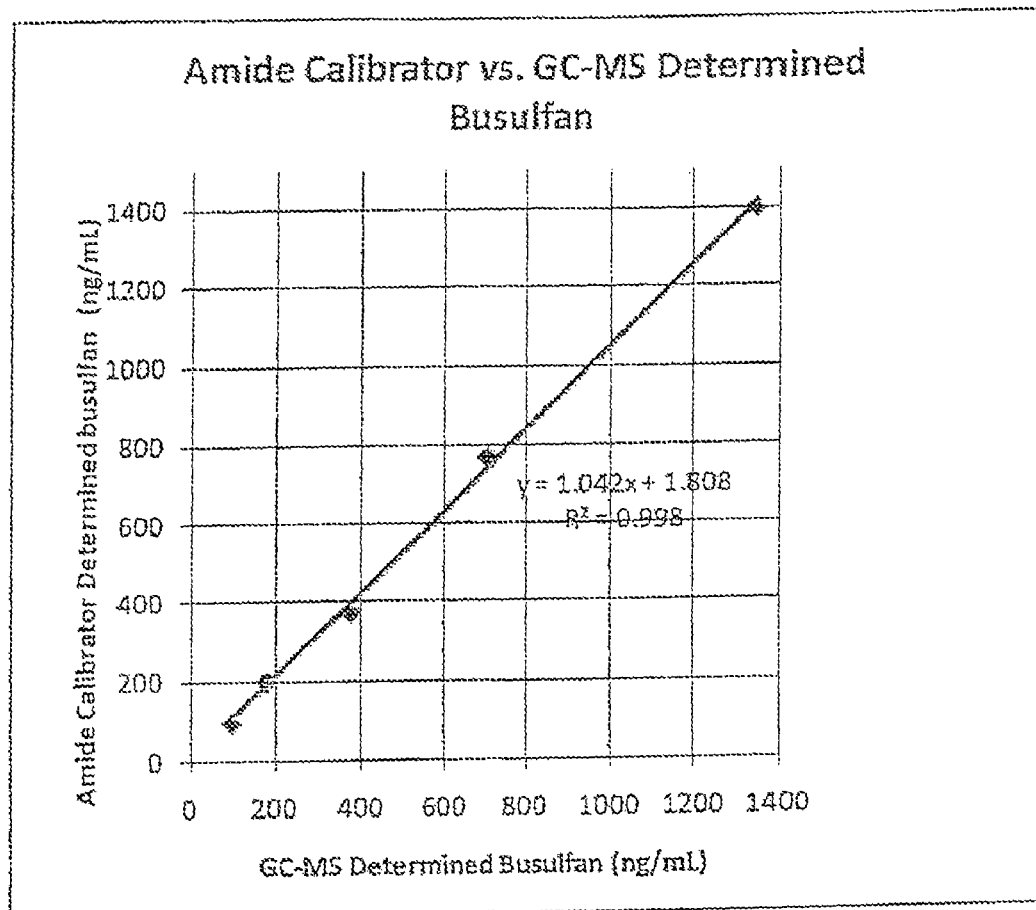
FIG. 3 is a graph demonstrating method of obtaining the busulfan equivalence facto from the calibration between the results of a busulfan immunoassay utilized various known concentrations of busulfan and these results obtained with various standards formed with the compounds of this invention and that the relationship and correspondence between both results across the entire dose response curve, produced a busulfan equivalence factor.

The fact that known concentrations of the amide of formula II can be calibrated with known concentrations of busulfan by means of a calibration assay can be seen from FIG. 3. As seen from FIG. 3, in calibrating the standards containing known concentrations of the amide of formula II with standards prepared with known concentrations of busulfan, various aqueous test solutions were prepared containing busulfan and the amide of Formula II. These test solutions are a set of standards formed from the amide of formula II and a set of standards formed from busulfan, each with known concentrations of busulfan or the amide of Formula II. The set of standards which contain busulfan and the set of standards of the amide are subjected to the same busulfan calibration immunoassay and the results measure the amount of busulfan in the set of busulfan standards and the amount of amide of Formula II in the amide standards. These measured results are plotted against their relative concentrations. As shown in FIG. 3, a plot is generated either in the form of a curve or a straight line. As seen from the plot in FIG. 3, it has been discovered that there is a constant calibration factor between the measured results of the busulfan standards with the measured results of the standards containing the amide Formula II across the entire dose response curve. When the assay of U.S. Pat. No. 7,148,024 is utilized, the stabilized derivative has a 17.5% relative cross reactivity as compared to busulfan across the entire dose response curve. The amount or concentration of busulfan can be determined from the measured amount or concentration standards containing the amide of formula II by multiplying the measured results obtained from these amide standards by previously determined calibration factor which in the case of FIG. 3 is 0.107. In this manner one obtains the amount or concentration of busulfan in the samples based on the measured results with respect to the amide.

This calibration factor will vary depending upon the specific immunoassay utilized. This factor is determined by the manufacturer or supplier before preparing the kit or submitting the reagents and materials to the healthcare facility for carrying out an immunoassay. Therefore there is no need for the manufacturer or supplier to provide kits to the health care facility with busulfan containing standards which are subject to deterioration after periods of standing. In carrying out the calibration immunoassay it is important to use the same immunoassay that will be used for the busulfan immunoassay of the sample for which the kit is supplied. This includes both the same reagents and same antibody and the same immunoassay technique to which the patents sample is subjected.

Usually these standards are supplied in the form of a inert liquid medium containing an inert solvent for the amide of formula II so that a given concentration of the amide of formula II is achieved. Any conventional inert liquid medium, including an inert solvent generally utilized in immunoassay standards, can be utilized in preparing the standards of this invention The components of the immunoassay, including the stabilizers, are provided in packaged combinations in a kit. The term "kit" refers to an assembly of materials that are used in performing the assay and in standardizing the results in performing the assay. The kit may contain the standards together with the reagents for performing the assay. On the other hand, the standards for calibrating the results of the assay may be provided in a separate kit. Where the standards are supplied in the same kit as the reagents for performing the assay, the kit contains the plurality of standards of different concentrations of the amide of formula II, each of these standards being supplied in a different container in packaged combinations either in liquid or lyophilized form. The number of separate standards and the concentration of the amounts of amide of formula II in the kit are selected so as to provide optimum results for a particular application, so as to provide the aforementioned plot as described here and before as a curve or a straight line. Therefore, the amount of standards will vary depending upon the particular immunoassay to which these standards are connected. If the standards present in the separate containers are in lyophilized form then at their point of their use, the liquid medium can be generated by adding solvents including buffers to provide a given concentration. What is important is that the sufficient standards in different concentration be supplied so that the results when subjected to the immunoassay to which they are connected generate a curve on a straight line which can be correlated to known concentrations of the results obtained with respect to busulfan as seen in FIG. 3. These kits of this invention may contain written instructions as to how to carry out an immunoassay. Also these written instructions may contain the aforementioned calibration factor or the standards may be labeled with a number can be labeled with the number obtained by multiplying the concentration of amide of Formula II in the standard with the predetermined busulfan equivalence factor. In this way the concentrations of the standards can be keep confidential since the number, rather than concentration, can be used in preparing the plot When the standards are packaged in kit for carrying out an immunoassay they, in a separate, with the reagents for carrying out the busulfan immunoassay to which they are connected. Any conventional reagent or other materials which are utilized in busulfan immunoassay can be utilized in this kit. Among the preferred reagents are the reagents disclosed in U.S. Pat. No. 7,148,024 which include the compounds of Formula III-A and III-B, if an antibody substantially selectively reacted with busulfan and not substantially cross reactive with tetramethylene sulfone, tetrahydrothiophene and tetrahydrothiophene-3-ol-1,1 dioxide. On the other hand the plurality of standards containing the amide of formula II can be provided in a calibration kit which contains in separate containers the plurality of these standards where the standards and concentrations vary in an amount and are supplied in amounts sufficient to provide a plot of the results of the immunoassay in which they are connected versus their concentration as a straight line or curve.

Throughout this description the following definitions are to be understood: The term "Me" as used throughout this application designates a methyl radical. The term "lower alkylene" designates a divalent saturated straight or branch chain hydrocarbon substituent containing from one to six carbon atoms. The term "lower alkenylene" designates a divalent straight or branch chain hydrocarbon group containing from two to six carbon atoms and an unsaturated double bond in the hydrocarbon chain.

The term "conjugate" refers to any substance formed from the joining together of two parts. Representative conjugates in accordance with the present invention include those formed by the joining together of a small molecule, such as the compound of formula II and a large molecule, such as a carrier or a polyamine polymer, particularly protein. In the conjugate the small molecule maybe joined at one or more active sites on the large molecule. The term conjugate includes the term immunogen.

"Haptens" are partial or incomplete antigens. They are protein-free substances, mostly low molecular weight substances, which are not capable of stimulating antibody formation, but which do react with antibodies. The latter are formed by coupling a hapten to a high molecular weight immunogenic carrier and then injecting this coupled product, i.e., immunogen, into a human or animal subject. The hapten of this invention is busulfan.

As used herein, a "spacing group" or "spacer" refers to a portion of a chemical structure which connects two or more substructures such as haptens, carriers, immunogens, labels, or tracers through a $CH_2$ or functional linking group. These spacer groups will be enumerated hereinafter in this application. The atoms of a spacing group and the atoms of a chain within the spacing group are themselves connected by chemical bonds.

Among the preferred spacers are straight or branched, saturated or unsaturated, carbon chains. Theses carbon chains may also include one or more hetero atoms within the chain or at termini of the chains. By "hetero atoms" is meant atoms other than carbon which are chosen from the group consisting of oxygen, nitrogen and sulfur. Spacing groups may also include cyclic or aromatic groups as part of the chain or as a substitution on one of the atoms in the chain.

The number of atoms in the spacing group is determined by counting the atoms other than hydrogen. The number of atoms in a chain within a spacing group is determined by counting the number of atoms other than hydrogen along the shortest route between the substructures being connected. A functional linking group may be used to activate, e.g., provide an available functional site on, a hapten or spacing group for synthesizing a conjugate of a hapten with a label or carrier or polyamine polymer.

An "immunogenic carrier," as the terms are used herein, is an immunogenic substance, commonly a protein, that can join with a hapten, in this case busulfan or the busulfan derivatives hereinbefore described, thereby enabling these hapten derivatives to induce an immune response and elicit the production of antibodies that can bind specifically with these haptens. The immunogenic carriers and the linking groups will be enumerated hereinafter in this application. Among the immunogenic carrier substances are included proteins, glycoproteins, complex polyamino-polysaccharides, particles, and nucleic acids that are recognized as foreign and thereby elicit an immunologic response from the host. The polyamino-polysaccharides may be prepared from polysaccharides using any of the conventional means known for this preparation. Also various protein types may be employed as a poly(amino acid) immunogenic carrier. These types include albumins, serum proteins, lipoproteins, etc. Illustrative proteins include bovine serum albumin (BSA), keyhole limpet hemocyanin (KLH), egg ovalbumin, bovine thyroglobulin (BTG) etc. Alternatively, synthetic poly(amino acids) may be utilized.

Immunogenic carriers can also include poly amino-polysaccharides, which are a high molecular weight polymer built up by repeated condensations of monosaccharides. Examples of polysaccharides are starches, glycogen, cellulose, carbohydrate gums such as gum arabic, agar, and so forth. The polysaccharide also contains polyamino acid residues and/or lipid residues. The immunogenic carrier can also be a poly(nucleic acid) either alone or conjugated to one of the above mentioned poly(amino acids) or polysaccharides.

The immunogenic carrier can also include solid particles. The particles are generally at least about 0.02 microns (μm) and not more than about 100 μm, and usually about 0.05 μm to 10 μm in diameter. The particle can be organic or inorganic, swellable or non-swellable, porous or non-porous, optimally of a density approximating water, generally from about 0.7 to 1.5 g/mL, and composed of material that can be transparent, partially transparent, or opaque. The particles can be biological materials such as cells and microorganisms, including non-limiting examples such as erythrocytes, leukocytes, lymphocytes, hybridomas, *Streptococcus, Staphylococcus aureus, E. coli*, and viruses. The particles can also be comprised of organic and inorganic polymers, liposomes, latex, phospholipid vesicles, or lipoproteins.

"Poly(amino acid)" or "polypeptide" is a polyamide formed from amino acids. Poly(amino acids) will generally range from about 2,000 molecular weight, having no upper molecular weight limit, normally being less than 10,000,000 and usually not more than about 600,000 daltons. There will usually be different ranges, depending on whether an immunogenic carrier or an enzyme is involved.

A "peptide" is any compound formed by the linkage of two or more amino acids by amide (peptide) bonds, usually a polymer of α-amino acids in which the α-amino group of each amino acid residue (except the $NH_2$ terminus) is linked to the α-carboxyl group of the next residue in a linear chain. The terms peptide, polypeptide and poly(amino acid) are used synonymously herein to refer to this class of compounds without restriction as to size. The largest members of this class are referred to as proteins.

A "label," "detector molecule," or "tracer" is any molecule which produces, or can be induced to produce, a detectable signal. The label can be conjugated to an analyte, immunogen, antibody, or to another molecule such as a receptor or a molecule that can bind to a receptor such as a ligand, particularly a hapten. Non-limiting examples of labels include radioactive isotopes, enzymes, enzyme fragments, enzyme substrates, enzyme inhibitors, coenzymes, catalysts, fluorophores, dyes, chemiluminescers, luminescers, or sensitizers; a non-magnetic or magnetic particle, a solid support, a liposome, a ligand, or a receptor.

The term "antibody" refers to a specific protein binding partner for an antigen and is any substance, or group of substances, which has a specific binding affinity for an antigen to the exclusion of other substances. The generic term antibody subsumes polyclonal antibodies, monoclonal antibodies and antibody fragments.

The term "derivative" refers to a chemical compound or molecule made from a parent compound by one or more chemical reactions.

The term "carrier" refers to solid particles and/or polymeric polymers such as immunogenic polymers such as those mentioned above. Where the carrier is a solid particle, the solid particle may be bound, coated with or otherwise attached to a polyamine polymer to provide one or more reactive sites for bonding to the terminal functional group X in the compounds of the formula II.

The term "reagent kit," or "test kit," refers to an assembly of materials that are used in performing an assay. The reagents can be provided, in packaged combination in the same or in separate containers, depending on their cross-reactivities and stabilities, and in liquid or in lyophilized form.

The term "human biological sample" or former living thing. Such living things include, but are not include, but are not limited to, blood, serum, plasma, urine, cells, organs, tissues, bone, bone marrow, lymph, lymph nodes, synovial tissue, chondrocytes, synovial macrophages, endothelial cells, and skin.

The preferred antibodies are produced by use of the procedure of U.S. Pat. No. 7,148,024 which is incorporated by the reference path are selective for busulfan without having any substantial cross-reactivity with the blocking metabolites of busulfan which are tetramethylene sulfone, tetrahydrothiophene and tetrahydrothiophene-3-ol-1,1-dioxide. By not having any substantial cross-reactivity, it is meant that the antibodies of this invention have a cross reactivity relative to busulfan with these blocking metabolites of less than 10%, preferably less than 5%.

EXAMPLES

Ph represents phenyl. In the examples, the following abbreviations are used for designating the following:
GC-MS Gas chromatograph mass spectrometry
$K_2CO_3$ Potassium carbonate
MeOH Methanol
HCl Hydrochloric acid
NaCl Sodium chloride
BSA Bovine serum albumin
PBS Phosphate buffered saline
ANS 8-Anilino-1-naphthalenesulfonic acid
HRP horse radish-peroxidase
TMB 3,3',5,5'-Tetramethylbenzidine
Thimerosal 2-(Ethylmercurimercapto)benzoic acid sodium salt
$NaN_3$ Sodium azide
di deionized water
Tween 80 Polyethylene glycol sorbitan monooleate
In the examples, "amide" designates the amide of formula II.

Example 1

Busulfan Calibrators

A stock solution of busulfan at 5 mg/mL in acetonitrile was prepared and stored in amber glass at −20° C. To prepared the six concentrations of the calibrators (75 ng/mL, 150 ng/mL, 300 ng/mL, 600 ng/mL, 1200 ng/mL, 2000 ng/mL)

the stock solution was diluted in a buffer comprising an aqueous buffer comprising 0.02 M sodium phosphate, 0.15 M NaCl, 0.1% BSA, 0.01% Thimerosal, pH 7.2. as follows: 0.1 mL of stock solution into 249.9 mL for final concentration of 20000 ng/mL busulfan; the 2000 ng/mL stock solution was then serially diluted with the above aqueous buffer to prepare the other concentrations. The final concentrations of the calibrators were verified by GC-MS.

Example 2

Synthesis of Stabilized Busulfan Amide Derivative

Note: The synthesis of the amide of formula II followed the procedure described by Johnston et al.*

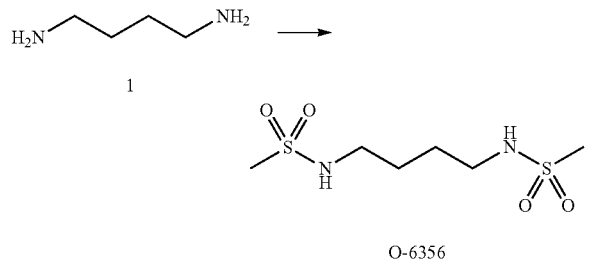

O-6356

Compound 1 (17.63 g, 200 mmol) was dissolved in anhydrous benzene (200 ml). $K_2CO_3$ (325 mesh, 60.8 g, 440 mmol) was added. A solution of methanesulfonyl chloride (34 mL, 440 mmol) in anhydrous benzene (100 ml) was added dropwise to the reaction mixture. A white precipitate was formed. The resulting suspension was heated to reflux. After 2 h the reaction mixture was allowed to cool, the white solid was collected by filtration, and was washed with benzene. After drying under high vacuum, the solid was triturated in water (250 ml), collected by filtration, and washed with water. The crude material was recrystallized from MeOH and from 1 M HCl (twice) to provide of the amide of formula II as substantially pave material (14.5 g, 30% yield).

Example 3

Preparation of Microliter Plate Coated with Anti-Busulfan Antibody

For the purpose of determining amide of formula II equivalents to busulfan of formula I and assaying busulfan with the amide standards by Enzyme-Linked Immunosorbent Assay (ELISA) method, polystyrene microtiter plates optimized for protein binding and containing 96 well per plate were used. Each well was coated with an antibody to busulfan produced as described in U.S. Pat. No. 7,238,024 Example 7, by adding 100 μL of antibody at 7.5 μg/mL in 0.05M sodium bicarbonate, pH=9.6 and then were blocked with 400 μL of 5% sucrose, 0.2% sodium caseinate solution for 30 minutes at room temperature. After removal of the post-coat solution the plates dried at 37° C. overnight.

Example 4

Determination of Amide Equivalents to Busulfan

The cross-reactivity of the amide was determined in a direct competitive Enzyme-Linked Immunosorbent Assay (ELISA) for busulfan. This method for measuring busulfan concentrations was performed with the microtiter plates that were sensitized with busulfan antibody described in Example 3. The amide stock solution at 6 mg/mL DMF was serially diluted 5000 ng/mL and 500 ng/mL in a buffer comprising 0.02 M sodium phosphate, 0.15 M NaCl, 0.1% BSA, 0.01% Thimerosal, pH 7.2. To perform the assay 30 μL of busulfan standards from Example 1, and 30 μL of amide of formula II dilutions were pre-diluted in a 96-well plate by the addition of 180 μL of sample pre-dilution buffer consisting of 0.02 M sodium phosphate, 0.15 M NaCl, 0.5% Dextran Sulfate, 0.01% Thimerosal, pH 7.2. 50 μL of all prediluted samples were added to the antibody coated microtiter plate of Example 3. After addition of the samples 50 μL of a busulfan-HRP conjugate at 100 ng/mL in a buffer comprising to 0.02 M sodium phosphate, 0.15 M NaCl, 0.2% BSA, 0.1% ANS (8-anilino-1-naphthalene sulfonic acid), 15 ppm ProClin® Preservative 300 was added. During the following 10 minute incubation (R.T., with shaking) there is a competition between sample (busulfan or amide) and busulfan-HRP for binding with the antibody in the well. Following this incubation the wells of the plate were washed three times with 0.02 M TRIS, 0.9% NaCl, 0.5% polyethylene glycol sorbitan monooleate TWEEN® 80 and 0.001% Thimerosal, pH 7.8 to remove any material that was not bound. To detect the amount of busulfan-HRP bound to the busulfan antibody in the wells, 100 μL of TMB (TMB Liquid Substrate) a substrate for HRP was added. To develop a measurable color in the wells there was a 10 second incubation (R.T., with shaking). Following the incubation 50 μL of stop solution comprising 1.5% sodium fluoride in di $H_2O$ was added to each well to stop the color development and after 10 seconds of shaking the absorbance was determined at 650 nm with a 96-well plate reader. The amount of busulfan-HRP in a well was proportional to the absorbance measured and inversely proportional to the amount of busulfan of formulated or amide of formulated in the sample. The absorbance of the color in the wells containing busulfan was compared to that with no busulfan analyte and a standard curve was generated. To calculate the cross-reactivity the amide concentration in the quantitative range was compared to its recovery compared to the busulfan standard: 537 ng/mL/5000 ng/mL=10.7% cross-reactivity. The cross-reactivity was used to determine the concentration of amide necessary to produce a calibration curve equivalent to that of busulfan (Example 6).

Example 5

Preparation of Stabilized Amide Standards

A stock solution of the amide as in Example 2 was prepared by dissolving the purified amide of formula II in dimethylformamide at a concentration of 40.06 mg/mL. The stock solution was diluted in a buffer comprising an aqueous buffer comprising 0.02 M sodium phosphate, 0.15 M NaCl, 0.1% BSA, 0.01% Thimerosal, pH 7.2. as follows: 0.235 mL of stock solution into 499.765 mL for final concentration of 18,800 ng/mL amide (II); the 18,800 ng/mL stock solution was then serially diluted with the above aqueous buffer to prepare the other concentrations; 11280 ng/mL, 5640 ng/mL, 2820 ng/mL, 1410 ng/mL, and 705 ng/mL. This corresponded to busulfan equivalence levels of a 2000 ng/mL stock, and 1200, 600, 300, 150, and 75 ng/mL respectively in the immunoassay for busulfan. These amide standards were then compared in the ELISA assay by running them as unknowns as described in the following Examples.

Example 6

Amide Calibration Compared to GC-MS Confirmed Busulfan Calibrators

Using the busulfan antibody plates (Example 3) in a direct competitive Enzyme-Linked Immunosorbent Assay (ELISA) for busulfan described in Example 4, the GC-MS verified busulfan calibrators (Example 1) were used to generate a curve from 75 ng/mL to 2000 ng/mL and the amide calibrators were read off this standard curve as unknown samples. FIG. 3 shows that the amide samples at concentrations of 705, 1410, 2820, 5640, 11280, and 18800 ng/mL gave the same absorbance values as the busulfan calibrators at 75, 150, 300, 600, 200 and 2000 meaning that the amide can be used to quantitate busulfan. The X axis represents the verified busulfan concentration and the Y axis is the amide standards expressed as busulfan equivalence factor (amide concentration value x 0.107=busulfan equivalence factor e.g. 1410 ng/mL amide x 0.107=150 ng/mL busulfan equivalence).

What is claimed:

1. A kit for determining the amount of busulfan in a patient's sample by means of a busulfan immunoassay comprising a plurality of standards in separate containers, each of the standards containing a different predetermined concentration or amount of an amide of the formula:

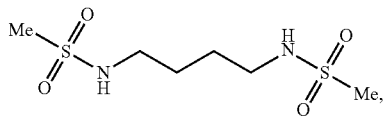

II and being packaged in separate containers and reagents for carrying out said busulfan immunoassay, said reagents being packaged in containers separate from those of said standards, wherein said reagents for carrying out said immunoassay comprise two separate containers, one of which containing an antibody which is selectively reactive with busulfan and not substantially cross-reactive with tetramethylene and tetrahydrothiophene-3-ol-1,1-dioxide and the other reagent being a conjugate of a polyamine polymer with a compound of the formula:

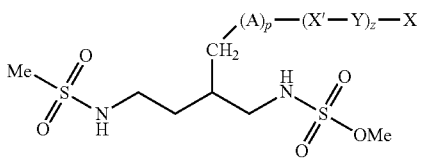

wherein A is lower alkylene;
X' is a functional linking group;
Y is an organic spacing group;
X is a terminal functional group capable of binding to said polyamine polymer;
p and z are independent integers from 0 to 1;
or a compound of the formula

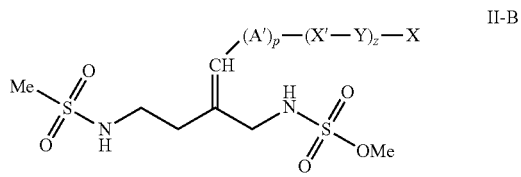

II-B wherein A' is lower alkyl or lower alkenylene.

2. The kit of claim 1 wherein said plurality of standards are in a number of at least three sufficient to generate a curve or a straight line by plotting the measured results obtained from said immunoassay of said standards against the concentration of said amide said standards.

3. The kit of claim 2 wherein each of the standards contains the amide of formula II in an inert liquid medium and the concentration of said amide in each of said standards is in the range of from 0 to 16,000 ng/ml.

* * * * *